United States Patent [19]

Matkovich et al.

[11] Patent Number: 5,334,315
[45] Date of Patent: Aug. 2, 1994

[54] PRIMING SYSTEM

[75] Inventors: Vlado I. Matkovich, Glen Cove; Thomas J. Bormann, Melville; Gerard R. DelGiacco, Yonkers, all of N.Y.

[73] Assignee: Pall Corporation, Glen Cove, N.Y.

[21] Appl. No.: 824,788

[22] Filed: Jan. 17, 1992

[51] Int. Cl.⁵ .............................. B01D 61/20
[52] U.S. Cl. ................... 210/641; 210/651; 210/136; 210/436
[58] Field of Search ............... 55/158; 435/1; 604/48, 604/35; 210/641, 436, 472, 104, 254, 651; 60/288, 667

[56] References Cited

U.S. PATENT DOCUMENTS

| | | | |
|---|---|---|---|
| 3,113,925 | 12/1963 | Rosaen | 210/436 X |
| 3,591,493 | 7/1971 | Zeineh | 210/644 |
| 3,934,982 | 1/1976 | Arp | 55/158 X |
| 3,940,058 | 2/1976 | Norris | 60/667 X |
| 4,137,168 | 1/1979 | Perrot | 210/104 X |
| 4,369,785 | 1/1983 | Rehkopf et al. | 604/35 X |
| 4,677,823 | 7/1987 | Hardy | 60/288 X |
| 4,868,121 | 9/1989 | Scharp et al. | 435/1 X |
| 4,885,084 | 12/1989 | Doyle | 210/254 X |
| 4,997,577 | 3/1991 | Stewart | 210/767 |
| 5,128,048 | 7/1992 | Stewart et al. | 210/749 |

FOREIGN PATENT DOCUMENTS

| | | |
|---|---|---|
| 0080680 | 6/1983 | European Pat. Off. . |
| 0098392 | 1/1984 | European Pat. Off. . |
| 0479187 | 4/1992 | European Pat. Off. . |
| WO911780 | 9/1991 | PCT Int'l Appl. . |

OTHER PUBLICATIONS

Biological Abstracts, vol. 84, 1987, Abstract No. 16637, Pagano, L. et al., "Spinal fluid . . . methotrexate."
Intensive Care Medicine (1990), 15 Supplement 1.
Journal of Neurological Science (1990), 98 (Supplement), pp. 261–262.
Eur Arch Psychiatry Clin Neurosci (1991) 241:69–72.
Eur Arch Psychiatry Clin Neurosci (1992) 241:73–76.
Infusionstherapie (1991), 18 (2) Supplement.

Primary Examiner—Frank Spear
Attorney, Agent, or Firm—Leydig, Voit & Mayer

[57] ABSTRACT

Processes and systems and methods for priming a fluid processing apparatus and for treating a fluid are disclosed.

33 Claims, 2 Drawing Sheets

PRIMING SYSTEM

TECHNICAL FIELD

This invention relates to a system, apparatus, and method for priming a fluid processing or treating device. The invention also relates to a system, apparatus and method for treating a fluid.

BACKGROUND OF THE INVENTION

There are a number of methods and devices for processing and/or treating various fluids. For example, a number of therapeutic protocols for pathophysiological conditions involve the removal of a bodily fluid from a patient, treating that fluid to remove an undesirable component, and returning it to the patient. However, fluid processing and/or treatment need not be limited to therapeutic applications. For example, water may be rendered potable by passing it through a filter that removes substances such as bacteria.

Nevertheless, these methods, and the devices utilized to carry them out, have been inefficient in that they may require extra time and/or effort for priming. Additionally, these devices may waste fluid since a portion of the fluid may be held up in the devices. This may be expensive since the fluid may be unrecoverable and/or incompletely processed. Additionally, an additional labor intensive effort may be required to retrieve the held up fluid. Furthermore, especially when a separate fluid treatment assembly or device is added to the system, the devices utilized may be awkward to use, or may compromise sterility by allowing the introduction of bacteria and/or air.

These problems involving cost, labor, sterility and time are magnified when the fluid is valuable, especially when only a limited amount is available. For example, a number of therapeutic and non-therapeutic protocols involve attaching an assembly to a individual, removing a bodily fluid (e.g., blood), treating the fluid, and returning it to the individual. Since the individual only has a finite amount of that fluid, it may be necessary to minimize loss, preferably with minimal additional effort.

Moreover, during such protocols it is important to maintain sterility without administering inappropriate substances such as air. Furthermore, since patient fluid treatment protocols may present some risk to the patient, the time and operator sophistication required to perform them should be minimized to decrease the risk to the patient.

In view of this, there is a demand for a system and method for easily, simply, and effectively, priming a fluid processing or treating device. The system and method should also provide these same advantages when a separate fluid treatment assembly or device is added to the system. Additionally, there is a growing need for a simple system and method of processing or treating various fluids to deplete deleterious or undesirable substances from these fluids, as well as for a system and method for administering them, e.g., to a patient, while minimizing loss of the fluid, and requiring minimal operator labor and sophistication. Moreover, particularly when the fluid is to be administered to a patient, there is a need for a system and method that minimizes risk to the patient by providing for quick priming and simple operation, while maintaining sterility, and without introducing inappropriate substances such as air.

SUMMARY OF THE INVENTION

The present invention relates to a device and method for priming a fluid processing or treating apparatus or system whereby a bypass assembly allows the efficient and effective priming of a fluid processing assembly, and whereby a vent allows the elimination of gas from the assembly.

The invention also relates to an apparatus and method for treating a fluid by passing the fluid through an apparatus according to the invention.

SPECIFIC DESCRIPTION OF THE INVENTION

In accordance with the present invention, a device for priming a fluid processing or treating apparatus or system includes a fluid treatment element, a bypass connected in parallel with the fluid treatment element, a differential pressure generator in communication with the fluid treatment element and the bypass, and at least one vent in communication with at least one of the fluid treatment element, differential pressure generator, and the bypass assembly. Additionally, the present invention provides a method for priming a fluid processing system.

The invention also relates to treating a fluid by passing the fluid through a previously primed porous medium which depletes a deleterious or undesirable substance from the fluid. The treated fluid may then be returned to the source, e.g., a patient.

Figure 1:
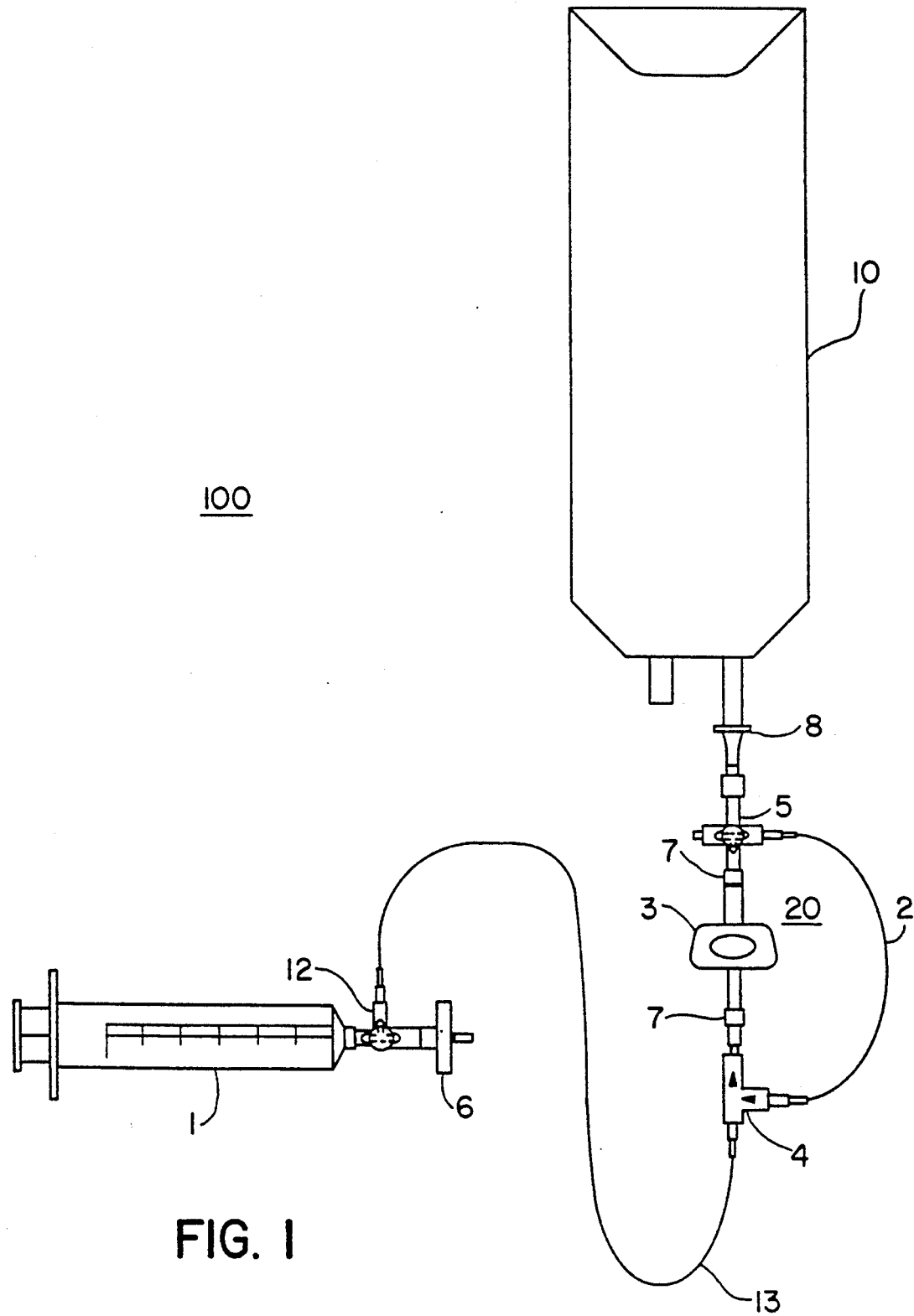
FIG. 1 is an embodiment of a priming and/or fluid processing system comprising an assembly according to the invention.

An exemplary system is shown in FIG. 1. Assembly 100, which is preferably a closed system, may include a differential pressure generator 1, in fluid communication with a fluid treatment element 3 and bypass assembly 20. In the illustrated embodiment, the bypass assembly 20 and the fluid treatment assembly 3 communicate with differential pressure generator 1 by different fluid flow paths through junctions 4 and 5. The assembly 100 may also include at least one vent 6, preferably communicating with the differential pressure generator 1 through junction 12. An assembly according to the invention may also include at least one flow control device; a conduit 2 connecting junction 4 with junction 5; a conduit 13 connecting junction 4 with junction 12; a variety of optional connectors 7, and a spike 8 or catheter connector (not shown), or the like, connected to the assembly 100. In the illustrated embodiment, spike 8 is connected to a container of priming fluid 10.

Each of the components of the invention will now be described in more detail below.

DIFFERENTIAL PRESSURE GENERATOR

The differential pressure generator 1 may be any container or device which may be used to generate a pressure differential in the assembly 100. Exemplary pressure differential generators include a pump, a flexible bag or a syringe. A syringe, and the like, is particularly preferred because it can be used to produce both a negative and a positive pressure differential, i.e., fluid can be drawn into the syringe and fluid can be expelled from the syringe. As long as the material used to make the differential pressure generator is suitable for use with the fluid being processed, any device used to pull or push fluid through a system is within the scope of the present invention.

The composition of the differential pressure generator may vary depending on the nature of the fluid or fluids utilized. Accordingly, it may be constructed of any material compatible with the fluid or fluids being passed through the system. Pressure differential generator 1 may be composed of a flexible material, for example, polyvinyl chloride (PVC), or plasticized PVC, e.g., PVC plasticized with dioctylphthalate, diethylhexylphthalate, or trioctyltrimellitate, each of which may be used in the construction of conventional blood bags. Alternatively, the differential pressure generator may be composed of a non-flexible material, for example, polypropylene, acrylonitrile butadiene styrene (ABS), polycarbonate, or stainless steel.

FLUID TREATMENT ELEMENT

The system 100 according to present invention also may include a fluid treatment element 3. It is intended that any device for treating and/or affecting the fluid, or performing some other desired function, is included within the scope of the invention. Typical fluid treatment elements include, but are not limited to, a bubble trap, a gas inlet, a gas outlet, an aerator, a pump, a column, a collection chamber or container, and the like. In a preferred embodiment, the fluid treatment element 3 is a filter assembly comprising a porous medium in a housing.

More preferably, the fluid treatment element is a filter assembly for removing one or more deleterious substances from the fluid. Exemplary fluid treatment elements include but are not limited to water treatment filters; filter assemblies for removing leucocytes from a fluid, such as a blood component; and filter assemblies for removing proteins and the like from a fluid such as cerebrospinal fluid.

The fluid treatment element 3 typically includes at least one inlet and at least one outlet which provide a flow path through the fluid treatment element. If the fluid treatment element includes a porous medium, the porous medium may be positioned across the flow path.

BYPASS ASSEMBLY

The bypass assembly 20, connected in assembly 100 in parallel with a fluid treatment element 3, may be any component or combination of components for bypassing a fluid treatment element 3. In accordance with the invention, a bypass assembly 20 may provide a fluid flow path around the fluid treatment element 3 (as illustrated), or may provide a separate, isolated fluid flow path through the fluid treatment element 3 (not shown).

Although the bypass assembly may be configured in a number of ways, the bypass assembly 20 preferably comprises a conduit 2, connecting junction 4 with junction 5, as illustrated in FIG. 1.

FLOW CONTROL DEVICE

The system 100 may also include at least one flow control device used to establish, control or direct the flow of fluid in a desired direction. Typical flow control devices include a clamp, seal, valve, transfer leg closure, stopcock, or the like. The flow control device may function automatically, e.g., a check valve, or it may be manually controlled, e.g., a stop cock or clamp.

The fluid flow control device or devices may be positioned in a variety of locations with respect to fluid flow. For example, a single fluid flow control device may be positioned to allow fluid to enter the differential pressure generator 1 without passing through the fluid treatment element 3. Alternatively, the flow control device may be positioned to allow fluid to flow through the fluid treatment element 3 without passing through the bypass assembly 20. Likewise, multiple flow control devices may be utilized for a similar effect. In a preferred embodiment, junctions 4 and 5 each include a flow control device. More preferably, junction 5 includes a rotatable three-way valve, and junction 4 includes two check valves.

Vent

A system 100 according to the invention also includes at least one vent 6 in communication with at least one of the fluid treatment element 3, the pressure differential generator 1, and the bypass assembly 20. The vent 6 may be positioned anywhere in the system 100, for example, in a conduit or in the fluid treatment element or the bypass assembly, for venting air or gas, and the like, from the system in order to prime the system and eliminate any extraneous gas. The vent 6 may include a conduit and/or a container, preferably a flexible bag, to which the air or gas can be delivered. In a preferred embodiment of the invention, the vent 6 is a gas outlet, preferably positioned in, on, or near the pressure differential generator 1. More preferably, vent 6 communicates with pressure differential 1 by junction 12, as shown in FIG. 1. Exemplary gas outlets are disclosed in WO 91/17809.

Flow to or through the vent may be regulated by a flow control device, such as a clamp, seal, valve, transfer leg closure, stopcock and the like. The regulation may be automatic, e.g., by a device or element that blocks flow when wetted. In a preferred embodiment, junction 12, which connects vent 6 to the system, includes a flow control device. More preferably, junction 12 includes a rotatable three-way valve.

The location of the vent 6 may be anywhere in the system 100, preferably positioned to provide the maximum amount of gas or air elimination from the assembly 100 during priming of the system. Preferably, the vent 6 is located between the differential pressure generator 1 and the bypass assembly 20, more preferably, downstream of the bypass assembly 20. Alternatively, the vent may be positioned in other locations to optimize a desired result. Preferably, the vent is chosen so that sterility is not compromised. More preferably, the vent may have a pore rating of about 0.2 micrometers or less to preclude bacteria from entering the assembly 100.

Additionally, the vent may be included in a housing, and/or may include a cap or closure.

Other materials and configurations for the vent are included within the scope of the present invention. For example, a puncturable, non-porous material may be used, e.g., to allow insertion of the needle of a syringe to withdraw the air from the system.

Typically, the various components of the assembly 100 have at least one connector 7 to facilitate connection to the other elements of the assembly. A variety of suitable conduits and connectors are known in the art.

METHOD

The invention also includes methods for priming a fluid processing apparatus wherein a priming fluid, for example, saline solution, is passed through the bypass assembly 20, through junction 4, and into pressure differential generator 1. The priming solution is then preferably directed through junction 4 and into and through fluid treatment element 3. At any point along the priming solution flow path, an appropriately placed vent may be opened in order to vent gas or air from the system.

An exemplary method according to the invention may be described with reference to FIG. 1. The assembly 100 is connected to a source of priming solution 10, such as a container of saline solution. As the plunger in the syringe is withdrawn, a pressure differential is created, drawing priming solution from the saline source container 10 into assembly 100. With the flow control device in junction 5 set to direct priming fluid into bypass assembly 20 and to block passage through the fluid treatment element 3, and the flow control device in junction 12 set to direct fluid into the syringe and to block passage through the vent 6, priming fluid and gas in the various components of the system pass into the bypass assembly 20, through junction 4, conduit 13 and junction 12 and into the syringe 1.

Once the gas and a desired amount of priming fluid is drawn into the syringe, setting the flow control device in junction 12 to direct flow toward the vent 6 and to block flow toward the bypass assembly 20 and the filter element 3, and partially depressing the plunger, allows gas to be expelled from the system through vent 6. Once the gas has been expelled, setting the flow control device in junction 12 to direct flow toward the bypass assembly 20 and the filter element 3, while blocking flow toward the vent 6, prevents gas from entering the system.

While the vent may be manually opened and closed, e.g., by capping or clamping, it may also be automatically controlled, e.g., the vent may include a device or element that passes gas until wetted by the priming fluid, and then blocks all flow.

With the flow control device in junction 5 set to allow priming fluid to flow through the fluid treatment element 3 and to block flow through the bypass, further depressing the plunger directs priming fluid from the syringe, through junction 4, and into the fluid treatment element 3. As the priming fluid flows through the fluid treatment element, it may displace gas and prime the fluid treatment element 3. The displaced gas, as well as priming fluid, may be directed through junction 5 back to the priming fluid bag.

Figure 2:
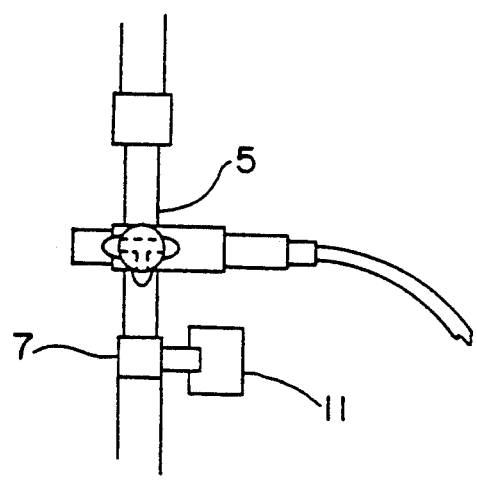
FIG. 2 is another embodiment of the invention showing a vent at the upstream junction.

Alternatively, as shown in FIG. 2, a vent 11 may be located on the fluid treatment element side of junction 5. With the fluid control device in junction 5 set to block flow through the fluid treatment element and the bypass, the priming fluid may be forced from the syringe into the fluid treatment element and the gas displaced from the fluid treatment element by the priming fluid may be expelled through the vent at the junction 5. Once the gas has been expelled through the vent, the vent may be closed and the flow control device at junction 5 may be set to block flow through the bypass and allow flow between the fluid treatment element and the priming fluid bag. The remaining priming fluid in the syringe may then be returned to the bag.

After priming, the assembly 100 may be disconnected from the source of priming fluid, and linked to the source of the fluid to be processed or treated.

Once connected to the source of the fluid to be processed or treated, the fluid can be drawn and passed through the primed assembly 100 in the same manner as described above for the priming fluid.

For example, if the fluid to be treated is water, it may be drawn through the primed assembly 100 in the same manner as described above for the priming fluid collecting treated water in a container. If additional processing or treatment is desired, this step may be repeated to recirculate the water through the assembly.

Similarly, an embodiment of the invention includes an apparatus and method for priming an administration assembly, treating a fluid, and introducing the treated fluid into a patient. For example, the fluid may be drawn through the primed assembly as described above. In this embodiment, the assembly 100 may include a connector or the like, e.g., a Y-connector, having one branch connected to the priming fluid bag, and the other connected to the patient. Once primed, the entire assembly can be connected to the patient.

Another embodiment of this invention includes an apparatus and method for priming an administration assembly, then collecting and treating a fluid from an individual (e.g., a donor or a patient), and then returning it to the individual, all while connected to the patient.

In a preferred embodiment of the invention, all of these functions can be performed without adding or deleting elements of the apparatus, thus maintaining a closed or sterile state.

For example, if the fluid to be treated is a fluid obtainable directly from a patient, the primed assembly 100 can be connected to the patient, by, for example, a catheter (not shown). Fluid can be drawn from the patient and passed through the primed assembly 100 in the same manner as described above for priming fluid.

In these embodiments of the invention, the fluid treatment element typically includes a porous medium for depleting a deleterious or undesirable substance or substances from a fluid. This generally means removing a therapeutically or clinically significant amount of a deleterious or undesirable substance from a fluid such as a biological fluid. "Therapeutically or clinically significant amount" refers to an amount necessary to produce a beneficial effect on the patient or animal receiving the substance-depleted fluid. Such a beneficial effect may be, for example, lessening a patient's symptoms.

Removal of a therapeutically or clinically significant amount can vary depending on the intended use and/or from patient to patient. For example, a therapeutically or clinically significant amount can be greater for a Guillain-Barré syndrome treatment protocol than a multiple sclerosis treatment protocol. However, removal of a therapeutically or clinically significant amount can be and is routinely determined by a doctor or technician for treating a certain condition or disease as it pertains to the specific patient, and as it pertains to the particular application.

These embodiments are applicable to a wide range of clinical or therapeutic regimens in which the depletion of deleterious or undesirable substances from the substance-containing fluid is beneficial. Although a comprehensive list would be too extensive to include here, among the deleterious or undesirable substances which may be depleted or removed for a beneficial effect include, but are not limited to, proteins, polypeptides, interleukins, immunoglobulins, proteases, interferon, tumor necrosis factor, complement, complement associated factors, gliotoxic factors, leucocytes, lymphocytes, and viruses. These substances may be found in an individual's fluids, e.g., cerebrospinal fluid (CSF), blood or blood component, urine, saliva, and the like.

one embodiment of the invention provides for treatment of Guillain-Barré syndrome. Guillain-Barré syndrome (acute polyradiculoneuropathy) is characterized by acute flaccid paralysis of muscles with associated muscle pains and paresthesia. In this embodiment, the cerebrospinal fluid (CSF) from a patient suffering from Guillain-Barré syndrome is passed through a previously primed assembly 100 and the deleterious or undesirable substance or substances associated with that syndrome are depleted from the fluid, which may be then returned to the patient. While not intending to be limited to any particular theory, it is believed that therapeutic benefit may be achieved by depleting proteins from the CSF. In this embodiment, it should be noted that the term "deleterious or undesirable substance" refers to both the singular and plural forms. Thus, e.g., a group of proteins is a deleterious or undesirable substance within the context of this invention. For convenience, the singular term "substance" will be used hereinafter, but it should be clear that the instant invention encompasses both the singular and plural forms.

With respect to this embodiment of the invention, the components of the apparatus 100 and the method of using it are generally as described previously.

The fluid treatment element 3 includes a porous depletion medium. Typically, the fluid treatment element may include a housing. The depletion medium may be formed from any natural or synthetic fiber or from a porous or permeable membrane (or from other materials of similar surface area and pore size) compatible with the fluid containing the deleterious or undesirable substance. The surface of the fibers or membrane may be unmodified or may be modified to achieve a desired property. Although the deleterious medium may remain untreated, the fibers or membrane are preferably treated with a charge modifying agent to produce a negatively or positively charged depletion medium. The charge-modified depletion medium may have negative or positive zeta potential. A charge neutral depletion medium may also be used in the instant invention.

While the depletion media can be produced from any material compatible with the fluid to be treated, practical considerations dictate that consideration be given first to the use of commercially available materials. The porous media of this invention may be preferably formed, for example, from a synthetic polymer. Suitable polymers include, but are not limited to, polyolefins, polyesters, polyamides, polysulfones, acrylics, polyacrylonitriles, polyaramides, polyarylene oxides and sulfides, and polymers and copolymers made from halogenated olefins and unsaturated nitriles. Examples include, but are not limited to, polyvinylidene fluoride, polyethylene, polypropylene, cellulose acetate, and Nylon 6 and 66. Preferred polymers are polyolefins, polyesters, and polyamides.

The depletion medium may be fashioned in a variety of ways to effectively deplete the deleterious or undesirable substance from the substance-containing liquid. For example, the depletion medium may be a porous web or sheet, membrane, fibrous mass, or depth filter. It may have a large surface area. The depletion medium may be suitable for ultrafiltration, e.g., an ultrafiltration membrane.

The depletion medium may be formed into any geometric shape, preferably pre-formed, suitable for passing a fluid therethrough. In a preferred embodiment, the depletion medium is a substantially rectangular pleated depth filter.

Preferably, the depletion medium of this embodiment of the invention is a sheet formed into a pleated, corrugated, or accordion form. Additionally, the depletion medium may comprise a composite or multilayer element, or, in a less preferable alternative, separate elements may be used independently in a series arrangement. The depletion medium may also include additional components, including, but not limited to at least one layer to provide support and/or better drainage. Exemplary supports and/or drainage components are non-woven polyester or polypropylene mesh.

The depletion medium may have a substantially constant pore rating or it may vary in a continuous or stepwise manner, particularly when multiple layers are utilized. For example, it may include pore ratings within the range of about 0.04 to about 40 micrometers, more preferably about 0.2 to about 5 micrometers.

Exemplary fluid treatment elements are disclosed in U.S. Pat. Nos. 4,702,840; 4,340,479; 4,855,163; 4,774,132; 4,906,374; 4,886,836; 4,964,989; and 4,707,266. When cerebrospinal fluid is the substance-containing fluid, media available from Pall Corporation under the trademark POSIDYNE ® are particularly preferred. Commercially available media, such as those available from Pall Corporation under the trademarks ULTIPOR ®, ULTIPOR N$_{66}$ ®, LOPRODYNE ®, FLUORODYNE ®, CARBOXYDYNE ®, and IMMUNODYNE ®, BIODYNE A ®, BIODYNE B ®, and BIODYNE C ®, may also be suitable.

As noted above, the fluid treatment element 3 may include a housing. Any housing of suitable shape to provide an inlet and an outlet may be employed. The housing may be fabricated from any suitably rigid, impervious material, including any impervious thermoplastic material, which is compatible with the fluid being processed. For example, the housing may be fabricated from a metal, such as stainless steel, or from a polymer. In a preferred embodiment, the housing is fabricated by injection molding from a polymer, more preferably a transparent or translucent polymer, such as an acrylic, polypropylene, polystyrene, or a polycarbonated resin. Not only is such a housing easily and economically fabricated, but also it allows observation of the passage of the liquid through the housing. The surfaces of the housing contacting the fluid may be treated or untreated. For example, the surfaces of the housing contacting the fluid may be rendered liquophilic for better priming. Methods for treating the surface of the housing include but are not limited to radiation grafting and gas plasma treatment.

The filter assembly in accordance with this invention may be fashioned in a variety of configurations. Housings can be designed to accept a variety of shapes of depletion media as long as adequate flow area is provided. All of these shapes are within the scope of the claimed invention.

The depletion medium may be sealed or fit within the housing to achieve convenience of use, rapid priming, and efficient air clearance. For example, the depletion medium may be compression sealed or interference fit within the housing. Alternatively, the housing may be overmolded, or heat welded, radiofrequency welded or ultrasonically welded. Additionally, a portion of the depletion medium may be located within the welds. Other suitable techniques for sealing or fitting the depletion medium within the housing are known to those skilled in the art.

In performing the method according to this embodiment of the invention, the flow rate of the patient's fluid is preferably sufficient to deplete a therapeutically or clinically significant amount of a deleterious or undesirable substance from the patient's fluid. The flow rate may depend on a number of variables, and thus, a range of rates are suitable. For example, the rate may vary from patient to patient, or from one type of fluid to another. Preferably, when the fluid is cerebrospinal fluid from a patient with Guillain-Barré syndrome, a volume of about 20 to about 40 ml is utilized for the cycle of collection, treatment and return.

As noted above, the present invention may be used in a wide range of clinical or therapeutic regimens in which depletion of a deleterious or undesirable substance is beneficial. Accordingly, the invention includes, but is not limited to treating pathophysiological conditions involving the nervous system, for example, Multiple Sclerosis and Amyotrophic Lateral Sclerosis; Acquired Immune Deficiency Syndrome (AIDS); dementia complex; encephalitis (e.g., HIV-I encephalitis); meningitis; polio; rabies; lyme disease; tetanus; diabetes; and infections by bacteria (e.g., borreliosis). However, other disorders may treated in this manner, e.g., autoimmune diseases such as Goodpasture's syndrome, rheumatoid arthritis, systemic lupus erythematosus, thyroiditis, myasthenia gravis, and anemia.

Suitable depletion media for these clinical or therapeutic regiments have been noted above. However, since the characteristics and composition of the depletion media may vary depending on the nature of the fluid, its intended use, and/or the pathophysiological condition being treated, other media may also be substituted or added.

Further embodiments are encompassed by the scope of the invention. In one embodiment, a unitary assembly is provided. In the context of the instant invention, unitary assembly refers to preassembled components that may be connected as a single unit to a fluid processing system or apparatus or to a patient. For example, a unitary assembly may refer to a fluid treatment element including at least one porous medium suitable for removing a deleterious or undesirable substance from a fluid, connected in parallel with a bypass. This unitary assembly may be pre-primed for ease of use in fluid processing.

In another embodiment, the bypass flow path may be a fluid flow path through the fluid treatment element 3.

While the present invention may be used to deplete a deleterious or undesirable substance directly from a fluid, the present invention may also be used therapeutically to deplete this substance indirectly. For example, since substances (e.g., proteins) may attach to a carrier, such as a leucocyte or a virus, the present invention may be used to deplete the fluid of the carrier, and thereby accomplish depletion of the deleterious or undesirable substance attached to the carrier. The present invention may be used to deplete a deleterious or undesirable substance from a fluid by immunoadsorption techniques. Such uses and devices are encompassed by the scope of the invention.

EXAMPLES

Example 1

The assembly used to perform this example may be set up in a manner that generally corresponds to that described for FIG. 1. The upstream junction of the bypass assembly includes a three-way valve, and the downstream junction of the bypass assembly includes two check valves. Additionally, a junction including a three-way valve is interposed between the differential pressure generator and the vent, and this junction is connected to the downstream junction of the bypass assembly by a flexible tube. Threaded connectors are used to connect these three junctions to the various components of the assembly. An apparatus according to the invention may be used in treating a patient suffering from Guillain-Barré Syndrome.

The differential pressure generator is a 60 cc plastic syringe, connected to the vent by the junction (which includes a three-way valve). This three-way valve (hereinafter the vent valve) provides for flow in and out of the syringe, and toward the vent or the bypass assembly and the fluid treatment element. The vent is a liquophobic polyamide membrane produced in accordance with WO 91/17809, with a pore rating of 0.2 micrometers to maintain a barrier to bacteria.

The fluid treatment element is a pleated, layered, microporous polyamide membrane sold under the tradename Posidyne ®, sealed into a substantially rectangular housing to form a filter assembly. The membrane includes a 0.8 micrometer layer downstream and a 0.2 micrometer layer upstream interposed between two polypropylene layers. The fluid treatment element in the housing (hereinafter the filter assembly) is connected to the junctions of the bypass assembly. The upstream junction of the bypass assembly includes a three-way valve as well as a threaded connector to provide for removable connection to a spike. The downstream junction of the bypass assembly includes a dual check valve, so that fluid will pass through the bypass to the syringe, but not vice-versa, and from the syringe to the filter assembly, but not into the bypass. This junction is connected to the syringe/vent junction by a flexible tube. The two junctions of the bypass assembly are also connected by a flexible tube to form a bypass loop.

With the exception of the syringe, all of the other elements of the assembly may be previously connected as a single unit. This single unit may be connected to the 60 cc syringe, with the plunger in the fully expelled position.

The spike may be placed in the saline pouch, and the three-way valve in the upstream junction of the bypass may be set so that fluid could flow through the bypass loop, but not to the filter assembly. The three-way vent valve may be rotated to provide for fluid flow to the syringe, but not to the vent.

The plunger of the syringe may be retracted to the 10 cc mark, and saline, pushing the air ahead of it, may pass through the bypass loop and into the syringe. The vent valve may then be rotated to allow fluid to flow to the vent, but not to the bypass and filter assembly. Air may be expelled by holding the syringe upright, and depressing the plunger approximately 3 cc until the air passes through the vent and the saline contacts the porous element of the vent.

The syringe, which now may contain about 7 cc of saline, may then be placed in a Harvard Apparatus Inc. programmable syringe pump, and operated according to the manufacturer's instructions. The vent valve may be rotated to block the flow path to the vent while opening the flow path leading to the filter assembly and the bypass. The first step of the Harvard automated procedure may be performed, and the syringe may be filled with an additional 25 cc of saline. The three-way valve in the upstream junction of the bypass assembly may be rotated to close the bypass loop and open the flow path leading through the filter assembly toward the saline pouch. The second step of the automated procedure may be run, which may prime the filter assembly with 30 cc of saline while forcing air into the saline pouch. The filter assembly may be gently tapped to help remove trapped air.

After the assembly is primed, the spike may be removed from the saline pouch, and disconnected from the fitting. The fitting may then be attached to the catheter which is connected to the patient. The three-way valve in the upstream junction of the bypass may be rotated to open both the bypass loop and the path through the filter assembly, while the check valve arrangement in the downstream junction of the bypass assembly is sufficient to resist flow through the filter assembly while allowing flow forward through the bypass and into the syringe. The third step of the automated procedure may be run, which may fill the syringe with 25 cc of cerebrospinal fluid (CSF) at a flow rate of less than about 2 cc per minute.

Since the check valve arrangement in the downstream junction of the bypass assembly resists flow backward through the bypass, and directs flow through the filter assembly, the fourth step of the procedure may be run, which may infuse 25 cc of CSF through the filter assembly and the catheter and back into the patient, at a flow rate of less than about 5 cc per minute. The third and fourth step may then be repeated, resulting in treating approximately 75 cc of spinal fluid.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

We claim:

1. A method for priming a fluid processing apparatus comprising:
   passing a priming fluid through a bypass connected in parallel with an unprimed fluid treatment element including at least one porous medium;
   venting gas from the fluid processing apparatus through a gas outlet comprising a porous element; and
   passing the priming fluid through the fluid treatment element and the porous medium.

2. The method of claim 1 wherein venting gas from the fluid processing apparatus comprises passing the gas displaced by the priming fluid in the bypass through the gas outlet.

3. The method of claim 1 wherein venting gas from the fluid processing apparatus comprises passing the gas displaced by the priming fluid in the fluid treatment element through the gas outlet.

4. The method of claim 1 wherein venting gas from the fluid processing apparatus comprises passing the gas displaced by the priming fluid in the bypass through a first gas outlet, and passing the gas displaced by the priming fluid in the fluid treatment element through a second gas outlet.

5. The method of claim 1 further comprising treating a fluid by passing it through the primed bypass and then the primed fluid treatment element.

6. The method of claim 5 wherein treating the fluid further comprises withdrawing the fluid from a patient and introducing the treated fluid back into the patient.

7. The method of claim 6 wherein withdrawing fluid from a patient comprises withdrawing cerebrospinal fluid.

8. The method of claim 1 comprising venting gas through a gas outlet comprising a bacterial blocking membrane.

9. The method of claim 1 wherein priming the apparatus includes creating a pressure differential sufficient to allow priming fluid to flow through the apparatus.

10. The method of claim 9 comprising creating a pressure differential utilizing a flexible differential pressure generator.

11. The method of claim 9 comprising creating a pressure differential utilizing a non-flexible differential pressure generator.

12. A method of depleting a deleterious or undesirable substance from a patient's fluid comprising:
    passing a priming fluid through a bypass connected in parallel with an unprimed fluid treatment element, wherein the fluid treatment element includes at least one porous medium suitable for removing a deleterious or undesirable substance from the patient's fluid;
    exhausting the gas displaced by the priming fluid through a vent;
    passing the priming fluid through the fluid treatment element;
    withdrawing a fluid containing a deleterious or undesirable substance from a patient through the primed bypass; and
    then passing the patient's fluid through the primed fluid treatment element to deplete the deleterious or undesirable substance from the fluid.

13. The method of claim 12 further comprising introducing the depleted fluid into the patient.

14. The method of claim 12 wherein withdrawing a fluid containing a deleterious or undesirable substance from a patient through the primed bypass and passing the patient's fluid through the primed fluid treatment element to deplete the deleterious or undesirable substance from the fluid comprises withdrawing cerebrospinal fluid from a patient through the primed bypass and passing it through the primed fluid treatment element.

15. The method of claim 14 further comprising introducing the depleted cerebrospinal fluid into the patient.

16. The method of claim 15 wherein introducing the depleted cerebrospinal fluid into the patient comprises introducing the cerebrospinal fluid depleted of the deleterious or undesirable substance associated with Guillain-Barré syndrome.

17. The method of claim 12 wherein exhausting the gas through the vent comprises passing gas through a gas outlet including a porous element.

18. A fluid processing device comprising:
    a fluid treatment element, which includes a porous medium;
    a bypass assembly connected in parallel with the fluid treatment element through a first junction and a second junction;
    a syringe in fluid communication with the second junction; and a gas outlet, which includes a bacterial barrier membrane, in fluid communication with the syringe through a vent junction.

19. The apparatus of claim 18 wherein the porous medium comprises a membrane.

20. The apparatus of claim 19 wherein the membrane has a surface area in the range of from about 15 to about 300 cm².

21. The apparatus of claim 19 wherein the membrane has a thickness in the range of from about 0.1 to about 1 mm.

22. The apparatus of claim 19 wherein the membrane has a pore rating in the range of about 0.04 to about 0.45 micrometers.

23. The device of claim 18 wherein the second junction includes a dual check valve, which allows fluid flow through the bypass to the syringe and from the syringe to the fluid treatment element and resists fluid flow backward through the bypass.

24. The device of claim 18 wherein the bacterial barrier membrane includes a liquophobic polyamide membrane.

25. The device of claim 18 wherein the porous medium includes a microporous membrane.

26. The device of claim 18 wherein the first junction includes a three-way valve and a connector;
the second junction includes a dual check valve, which allows fluid flow through the bypass to the syringe and from the syringe to the fluid treatment element and resists fluid flow backward through the bypass;
the vent junction includes a three-way valve connected to the second junction by a flexible tube;
the porous medium comprises a microporous polyamide membrane; and
the bacterial barrier membrane comprises a liquophobic polyamide membrane having a pore rating of about 0.2 micrometer.

27. The device of claim 18 wherein the fluid treatment element includes an inlet and an outlet, with the porous medium across the fluid flow path between the inlet and the outlet.

28. The device of claim 27 wherein the porous medium comprises a pleated medium.

29. A method for processing cerebrospinal fluid comprising:
passing a priming fluid through a bypass connected in parallel with an unprimed fluid treatment element including at least one porous medium;
venting gas;
passing the priming fluid through the porous medium of the fluid treatment element; and
passing cerebrospinal fluid through the bypass and then through the primed porous medium to treat the cerebrospinal fluid.

30. The method of claim 29 wherein passing the priming fluid through the bypass comprises passing the priming fluid through a first junction, a conduit, and then a second junction to bypass the fluid treatment element; and,
wherein passing the priming fluid through the unprimed fluid treatment element comprises passing the priming fluid through the second junction and then the first junction to prime the fluid treatment element.

31. The method of claim 30 wherein passing the cerebrospinal fluid through the bypass and the primed porous medium comprises passing the cerebrospinal fluid through the first junction, the conduit, and the second junction to bypass the fluid treatment element, and then passing the cerebrospinal fluid through the second junction, the primed porous medium, and the first junction.

32. The method of claim 30 including passing priming fluid from a container through the bypass and then through the porous medium of the fluid treatment element back into the container to prime the fluid treatment element.

33. The method of claim 32 wherein venting gas comprises passing the gas through a gas outlet including a bacterial blocking membrane.

* * * * *